United States Patent
Okamoto et al.

(10) Patent No.: US 10,902,986 B2
(45) Date of Patent: Jan. 26, 2021

(54) SENSOR, MICROPHONE, AND TOUCH PANEL

(71) Applicant: KABUSHIKI KAISHA TOSHIBA, Tokyo (JP)

(72) Inventors: Kazuaki Okamoto, Yokohama Kanagawa (JP); Yoshihiko Fuji, Kawasaki Kanagawa (JP); Shiori Kaji, Kawasaki Kanagawa (JP); Yoshihiro Higashi, Komatsu Ishikawa (JP); Tomohiko Nagata, Yokohama Kanagawa (JP); Shotaro Baba, Kawasaki Kanagawa (JP); Michiko Hara, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 323 days.

(21) Appl. No.: 16/119,008

(22) Filed: Aug. 31, 2018

(65) Prior Publication Data
US 2019/0272934 A1 Sep. 5, 2019

(30) Foreign Application Priority Data
Mar. 1, 2018 (JP) .................................. 2018-036470

(51) Int. Cl.
*H01F 10/32* (2006.01)
*H01L 43/02* (2006.01)
(Continued)

(52) U.S. Cl.
CPC ..... *H01F 10/3259* (2013.01); *A61B 5/02141* (2013.01); *G01L 9/0051* (2013.01);
(Continued)

(58) Field of Classification Search
CPC . H01F 10/3259; H01F 10/3272; H01L 43/08; H01L 43/02; H01L 43/10;
(Continued)

(56) References Cited

U.S. PATENT DOCUMENTS 6,690,163 B1 2/2004 Hoshiya et al.
8,059,374 B2 11/2011 Zhao et al.
(Continued)

FOREIGN PATENT DOCUMENTS

JP 2000-215414 A 8/2000
JP 2009-81216 A 4/2009
(Continued)

*Primary Examiner* — Suman K Nath
(74) *Attorney, Agent, or Firm* — Finnegan, Henderson, Farabow, Garrett & Dunner, L.L.P.

(57) ABSTRACT

According to one embodiment, a sensor includes a deformable film portion, and a first sensing element provided at the film portion. The first sensing element includes a first magnetic layer, a second magnetic layer, and a first intermediate layer provided between the first and second magnetic layers. The first intermediate layer is nonmagnetic. The first magnetic layer includes a first film including Fe and Co, a second film including Fe and Co, a third film, and a fourth film. The third film includes at least one selected from the group consisting of Cu, Au, Ru, Ag, Pt, Pd, Ir, Rh, Re, and Os and is provided between the first and second films. The fourth film includes at least one selected from the group consisting of Mg, Ca, Sc, Ti, Sr, Y, Zr, Nb, Mo, Ba, La, Hf, Ta, and W and is provided between the third and second films.

19 Claims, 11 Drawing Sheets

(51) Int. Cl.
  *H01L 43/10* (2006.01)
  *A61B 5/021* (2006.01)
  *G01L 9/00* (2006.01)
  *H01L 43/08* (2006.01)
  *H01L 41/12* (2006.01)
  *H01L 41/16* (2006.01)
  *G06F 3/041* (2006.01)
  *H04R 1/02* (2006.01)

(52) U.S. Cl.
  CPC ............ *H01L 41/125* (2013.01); *H01L 41/16* (2013.01); *H01L 43/02* (2013.01); *H01L 43/08* (2013.01); *H01L 43/10* (2013.01); *A61B 2562/0247* (2013.01); *G06F 3/041* (2013.01); *H04R 1/028* (2013.01)

(58) Field of Classification Search
  CPC ....... H01L 41/125; H01L 41/16; H04R 1/028; G01L 9/0051; G01L 1/183; G06F 3/041; G06F 3/04144; A61B 5/02141; A61B 2562/0247
  See application file for complete search history.

(56) References Cited

U.S. PATENT DOCUMENTS

| | | | |
|---|---|---|---|
| 9,618,411 | B2 | 4/2017 | Yuasa et al. |
| 2006/0262460 | A1* | 11/2006 | Ide .................... H01F 10/3295 360/324.12 |
| 2009/0080238 | A1 | 3/2009 | Yoshikawa et al. |
| 2011/0295128 | A1 | 12/2011 | Yuasa et al. |
| 2014/0299950 | A1* | 10/2014 | Kim .................... G11C 11/161 257/421 |
| 2016/0009545 | A1 | 1/2016 | Fuji et al. |
| 2016/0268501 | A1* | 9/2016 | Kitagawa ............... H01L 43/08 |

FOREIGN PATENT DOCUMENTS

| | | |
|---|---|---|
| JP | 2010-166051 A | 7/2010 |
| JP | 2013-165977 A | 8/2013 |
| JP | 2014-52360 A | 3/2014 |

* cited by examiner

SENSOR, MICROPHONE, AND TOUCH PANEL

CROSS-REFERENCE TO RELATED APPLICATIONS

This application is based upon and claims the benefit of priority from Japanese Patent Application No. 2018-036470, filed on Mar. 1, 2018; the entire contents of which are incorporated herein by reference.

FIELD

Embodiments described herein relate generally to a sensor, a microphone, a blood pressure sensor, and a touch panel.

BACKGROUND

A sensor that uses a magnetic layer has been proposed. For example, the sensor is applied to a microphone, a blood pressure sensor, a touch panel, etc. It is desirable for the sensor to have high sensitivity.

DETAILED DESCRIPTION

Figure 1:
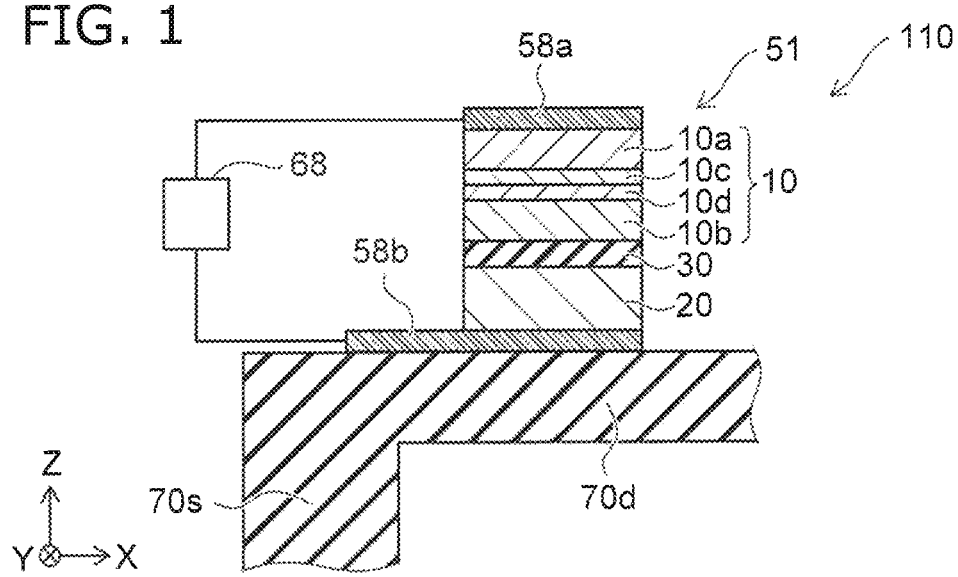
FIG. 1 is a schematic cross-sectional view illustrating a sensor according to a first embodiment.

According to one embodiment, a sensor includes a deformable film portion, and a first sensing element provided at the film portion. The first sensing element includes a first magnetic layer, a second magnetic layer, and a first intermediate layer provided between the first magnetic layer and the second magnetic layer. The first intermediate layer is nonmagnetic. The first magnetic layer includes a first film including Fe and Co, a second film including Fe and Co, a third film, and a fourth film. The third film includes at least one selected from the group consisting of Cu, Au, Ru, Ag, Pt, Pd, Ir, Rh, Re, and Os and is provided between the first film and the second film. The fourth film includes at least one selected from the group consisting of Mg, Ca, Sc, Ti, Sr, Y, Zr, Nb, Mo, Ba, La, Hf, Ta, and W and is provided between the third film and the second film.

According to another embodiment, a microphone includes the sensor described above.

According to another embodiment, a blood pressure sensor includes the sensor described above.

According to another embodiment, a touch panel includes the sensor described above.

Various embodiments will be described hereinafter with reference to the accompanying drawings.

The drawings are schematic and conceptual; and the relationships between the thickness and width of portions, the proportions of sizes among portions, etc., are not necessarily the same as the actual values thereof. Further, the dimensions and proportions may be illustrated differently among drawings, even for identical portions.

In the specification and drawings, components similar to those described or illustrated in a drawing thereinabove are marked with like reference numerals, and a detailed description is omitted as appropriate.

First Embodiment

FIG. 1 is a schematic cross-sectional view illustrating a sensor according to a first embodiment.

As shown in FIG. 1, the sensor 110 according to the embodiment includes a film portion 70d and a first sensing element 51.

The film portion 70d is deformable. For example, the film portion 70d is supported by a supporter 70s. The film portion 70d deforms according to a force (e.g., sound, etc.) applied to the film portion 70d. The film portion 70d may be a cantilever beam or a fixed beam.

The first sensing element 51 is provided at the film portion 70d. The first sensing element 51 is provided at a portion of the film portion 70d. The portion is, for example, a portion of the film portion 70d proximal to the supporter 70s.

The first sensing element 51 includes a first magnetic layer 10, a second magnetic layer 20, and a first intermediate layer 30. The first magnetic layer 10 and the second magnetic layer 20 are, for example, ferromagnetic layers.

In this specification, "magnetic layer" may include a magnetic film and a nonmagnetic film stacked with each other. A portion that includes the stacked magnetic film and nonmagnetic film has a magnetization. The portion that includes the stacked magnetic film and nonmagnetic film is included in the "magnetic layer."

The first intermediate layer 30 is provided between the first magnetic layer 10 and the second magnetic layer 20. The first intermediate layer 30 is, for example, nonmagnetic. The first intermediate layer includes, for example, Mg—O, etc. Other examples of the first intermediate layer are described below.

The first magnetic layer 10 includes first to fourth films 10a to 10d. The first film 10a includes Fe and Co. The first film 10a is, for example, an FeCo film.

The second film 10b includes Fe and Co. The second film 10b may further include B. The second film 10b is, for example, a CoFeB film.

The third film 10c is provided between the first film 10a and the second film 10b. The third film 10c includes at least one selected from the group consisting of Cu, Au, Ru, Ag, Pt, Pd, Ir, Rh, Re, and Os. The third film 10c is, for example, a Cu film.

The fourth film 10d is provided between the third film 10c and the second film 10b. The fourth film 10d includes at least one selected from the group consisting of Mg, Ca, Sc, Tl, Sr, Y, Zr, Nb, Mo, Ba, La, Hf, Ta, and W. The fourth film 10d is, for example, a Ta film.

The direction from the second film 10b toward the first film 10a is taken as a first direction. The first direction is taken as a Z-axis direction. One direction perpendicular to the Z-axis direction is taken as an X-axis direction. A direction perpendicular to the Z-axis direction and the X-axis direction is taken as a Y-axis direction.

For example, the first to fourth films 10a to 10d recited above spread along the X-Y plane. For example, the film portion 70d recited above spreads along the X-Y plane. In the example, the second magnetic layer 20 is provided between the first magnetic layer 10 and the film portion 70d. The first magnetic layer 10 may be provided between the second magnetic layer 20 and the film portion 70d.

As shown in FIG. 1, a first electrode 58a and a second electrode 58b are provided in the example. The first magnetic layer 10, the second magnetic layer 20, and the first intermediate layer 30 are provided between these electrodes. A processor 68 is electrically connected to these electrodes.

The electrical resistance of the first sensing element 51 changes according to the deformation of the film portion 70d. For example, the change of the electrical resistance of the first sensing element 51 corresponds to the change of the electrical resistance between the first electrode 58a and the second electrode 58b. For example, the change of the electrical resistance of the first sensing element 51 corresponds to the change of the electrical resistance between the first magnetic layer 10 and the second magnetic layer 20.

For example, the change of the electrical resistance corresponds to the change of the angle between the magnetization of the first magnetic layer 10 and the magnetization of the second magnetic layer 20. For example, the orientation of the magnetization of the first magnetic layer 10 changes according to the deformation of the film portion 70d. For example, this is based on the magnetostriction. For example, the first magnetic layer 10 functions as a free magnetic layer.

On the other hand, for example, the orientation of the magnetization of the second magnetic layer 20 changes less easily than the orientation of the magnetization of the first magnetic layer 10. For example, the orientation of the magnetization of the second magnetic layer 20 substantially does not change when the film portion 70d deforms. For example, the second magnetic layer 20 functions as a fixed magnetic layer.

The angle between the magnetization of the first magnetic layer 10 and the magnetization of the second magnetic layer 20 changes when the film portion 70d deforms. The electrical resistance between the first magnetic layer 10 and the second magnetic layer 20 changes according to the change of this angle. For example, the change of the electrical resistance is based on a MR effect.

Thus, in the sensor 110 according to the embodiment, the deformation of the film portion 70d can be detected using the change of the electrical resistance of the first sensing element 51. The processor 68 detects a value corresponding to the change of the electrical resistance (at least one of a change of an electrical resistance, a change of a current, or a change of a voltage).

The sensor 110 is, for example, a pressure sensor. The sensor 110 is, for example, a magnetic device. The second magnetic layer 20 also may be a free magnetic layer in the description recited above.

In the sensor 110, the detection sensitivity of the deformation of the film portion 70d is dependent on a magnetostriction constant $\lambda$, a coercivity Hc, a MR ratio, etc. For example, in the case where the magnetostriction constant $\lambda$ is high, the orientation of the magnetization of the magnetic layer changes easily with respect to the deformation of the film portion 70d. The orientation of the magnetization changes easily when the coercivity Hc is small. In the case where the MR ratio is high, the change of the electrical resistance is large with respect to the change of the angle between the two magnetizations.

In the embodiment, the first magnetic layer 10 includes the first to fourth films 10a to 10d recited above. Thereby, as described below, for example, a high magnetostriction constant is obtained. For example, a small coercivity Hc is obtained. For example, a high MR ratio is obtained. For example, a sensor can be provided in which the sensitivity can be increased.

Experiments performed by the inventor will now be described.

Figure 2:
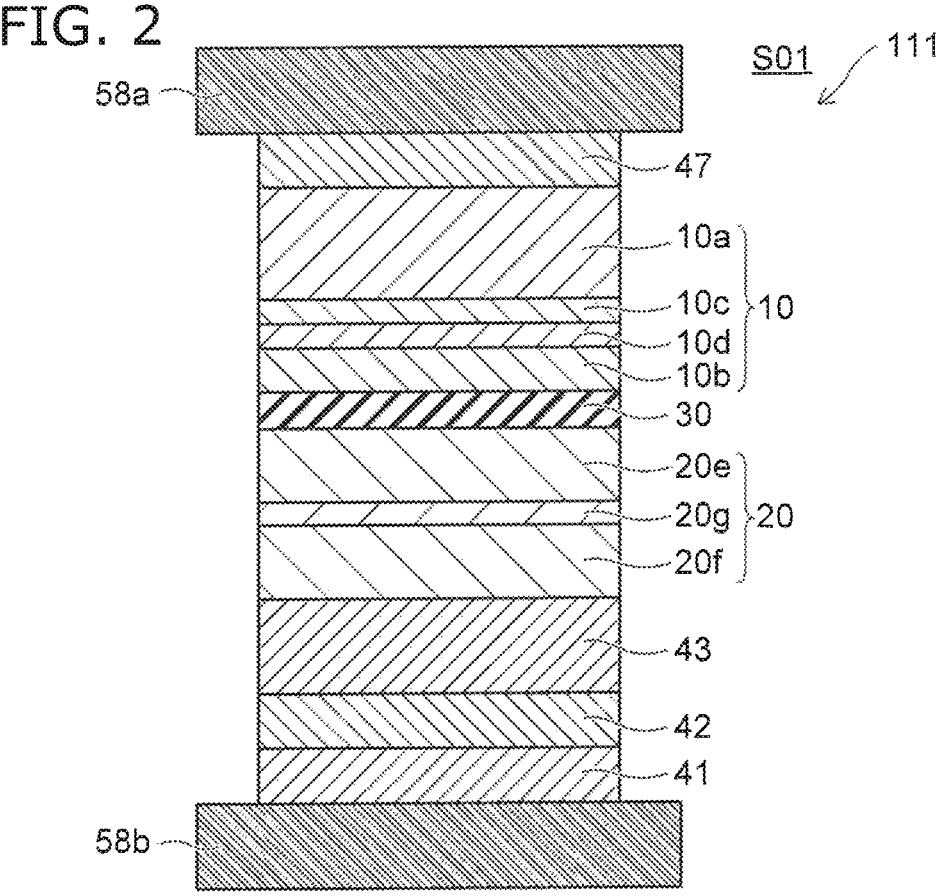
FIG. 2 is a schematic cross-sectional view illustrating an experiment sample.

FIG. 2 is a schematic cross-sectional view illustrating an experiment sample.

In the first sample S01 of the experiment as shown in FIG. 2, a film 41, a film 42, a third magnetic layer 43, the second magnetic layer 20, the first intermediate layer 30, the first magnetic layer 10, and a film 47 are provided in this order between the first electrode 58a and the second electrode 58b. In the example, the second magnetic layer 20 includes a fifth film 20e, a sixth film 20f, and a seventh film 20g. The fifth film 20e is provided between the sixth film 20f and the first intermediate layer 30. The seventh film 20g is provided between the fifth film 20e and the sixth film 20f.

The configuration of the sample S01 is as follows. In the following description, the numerals inside the parentheses are thicknesses.

Film 41: Ta (1 nm)
Film 42: Ru (2 nm)
Third magnetic layer 43: $Ir_{22}Mn_{78}$ (7 nm)
Sixth film 20f: $Co_{50}Fe_{50}$ (2.5 nm)
Seventh film 20g: Ru (0.9 nm)
Fifth film 20e: $Co_{40}Fe_{40}B_{20}$ (3 nm)
First intermediate layer 30: Mg—O (1.8 nm)
Second film 10b: $Co_{40}Fe_{40}B_{20}$ (1.5 nm)
Fourth film 10d: Ta (0.4 nm)
Third film 10c: Cu (0.4 nm)
First film 10a: $Co_{50}Fe_{50}$ (6.0 nm)
Film 47: Mg—O (1.5 nm)/Cu (1 nm)/Ta (2 nm)/Ru (200 nm)

In the film 47, the Ta film is provided between the Ru film and the first film 10a. The Cu film is provided between the Ta film and the first film 10a. The Mg—O film is provided between the Cu film and the first film 10a.

The second electrode 58b has a stacked structure of a first Ta film (3 nm)/Cu film (33 nm)/second Ta film (20 nm). The second Ta film is provided between the Cu film and the film 41.

The magnetization of the fifth film 20e and the magnetization of the sixth film 20f are magnetically coupled to each other. For example, the magnetization of the fifth film 20e and the magnetization of the sixth film 20f are antiparallel.

For example, the first sample S01 corresponds to a sensor 111 according to the embodiment.

The fourth film 10d (the Ta film) is not provided in a second sample S02. The third film 10c (the Cu film) is not provided in a third sample S03. Otherwise, the configurations of the second sample S02 and the third sample S03 are the same as that of the first sample S01.

Heat treatment in a magnetic field is performed at 320° C. for 1 hour for each of the first to third samples S01 to S03. The magnitude of the magnetic field applied in the heat treatment is 6500 oersteds.

The magnetization characteristics of the first to third samples S01 to S03 after the heat treatment are measured using a vibrating-sample magnetometer (VSM). In the VSM measurements, an external magnetic field H is applied; and a magnetic moment M of the sample is determined. The external magnetic field H is changed one oscillation between +250 Oe to −250 Oe (a low magnetic field). The planar configuration is a square for the first to third samples S01 to S03. The length of one side of the square is 10 mm.

Figure 3A:
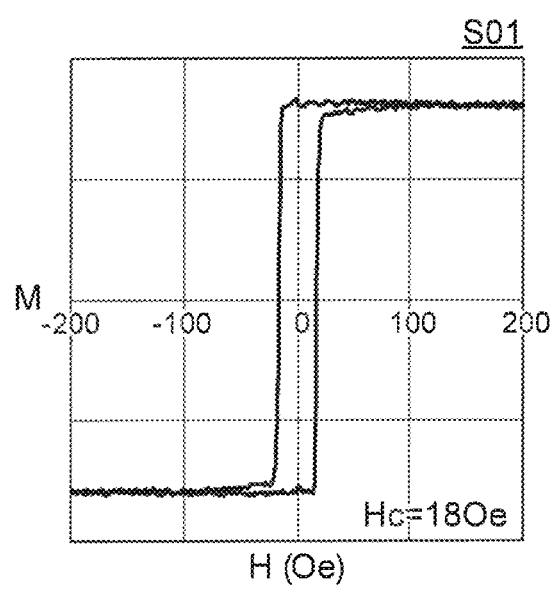
FIG. 3A to FIG. 3C are graphs illustrating characteristics of the sensors.
Figure 3B:
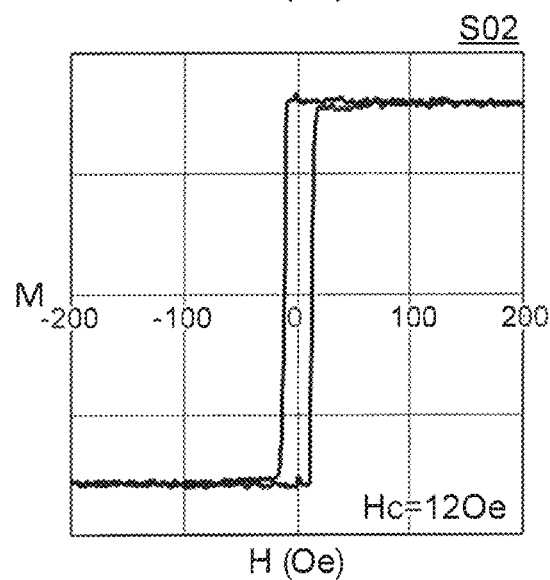
Figure 3C:
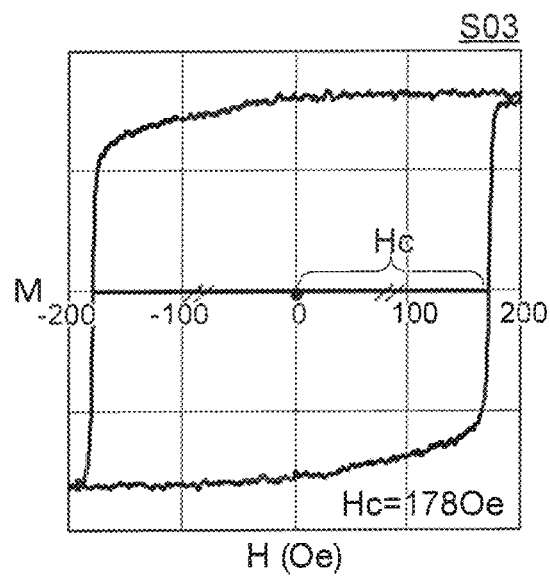

FIG. 3A to FIG. 3C are graphs illustrating characteristics of the sensors.

FIG. 3A to FIG. 3C correspond respectively to the first to third samples S01 to S03. In these figures, the horizontal axis is the external magnetic field H (Oe). The vertical axis is the magnetic moment M.

The saturation magnetization of the $Co_{50}Fe_{50}$ included in the first film 10a is about 2.1 T (teslas). The magnetic thickness (the product of the saturation magnetization and the thickness) of the first film 10a is 2.1 T×6 nm, i.e., 12.6 Tnm. On the other hand, the saturation magnetization of the $Co_{40}Fe_{40}B_{20}$ included in the second film 10b is about 1.9 T. The magnetic thickness (the product of the saturation magnetization and the thickness) of the second film 10b is 1.9 T×1.5 nm, i.e., 2.85 Tnm. The magnetic thickness of the first film 10a is not less than 4.4 times the magnetic thickness of the second film 10b. Accordingly, it is considered that the change of the magnetic moment M shown in FIG. 3A to FIG. 3C corresponds mainly to the change of the magnetic moment of the first film 10a.

As shown in FIG. 3A to FIG. 3C, compared to the first sample S01 and the second sample S02, the coercivity Hc is large for the third sample S03. The coercivity Hc of the first sample S01 is 18 Oe. The coercivity Hc of the second sample S02 is 12 Oe. The coercivity Hc of the third sample S03 is 178 Oe.

For example, it is considered that the coercivity Hc can be maintained to be small by providing the third film 10c (the Cu film). For example, it is considered that the coercivity Hc of the first film 10a (the $Co_{50}Fe_{50}$ film) can be reduced by providing the third film 10c (the Cu film).

The measurement results of the MR ratio and the magnetostriction constant for the first to third samples S01 to S03 recited above will now be described. The MR ratio is measured by CIPT (Current In-Plane-Tunneling). The magnetostriction constant is measured by observing the change of the anisotropic magnetic field when applying strain.

The MR ratio of the first sample S01 is 149%. The magnetostriction constant of the first sample S01 is 42.2 ppm.

The MR ratio of the second sample S02 is 17%. The magnetostriction constant of the second sample S02 is 42.6 ppm.

The MR ratio of the third sample S03 is 150%. The magnetostriction constant of the third sample S03 is 40.7 ppm.

From the results recited above, it is considered that a high MR ratio is obtained by providing the fourth film 10d (the Ta film). For example, in the first sample S01 and the third sample S03, the second film 10b (the $Co_{40}Fe_{40}B_{20}$ film) is provided between the fourth film 10d (the Ta film) and the first intermediate layer 30 (the Mg—O film). In the first sample S01 and the third sample S03, it is considered that the second film 10b is crystallized using the (100) plane of the first intermediate layer 30 as a template. Thereby, in the first sample S01 and the third sample S03, it is considered that a high MR ratio is obtained. For example, it is considered that the fourth film 10d (the Ta film) promotes (or does not obstruct) the crystallization of the second film 10b using the first intermediate layer 30 as a template.

On the other hand, in the second sample S02, the second film 10b (the $Co_{40}Fe_{40}B_{20}$ film) is provided between the third film 10c (the Cu film) and the first intermediate layer 30 (the Mg—O film). In the second sample S02, there is a possibility that the second film 10b may be crystallized using the third film 10c (the Cu film) as a template. For example, there is a possibility that the third film 10c (the Cu film) may obstruct the crystallization of the second film 10b using the first intermediate layer 30 as a template.

As recited above, a high magnetostriction constant and a low coercivity Hc are obtained in the first sample S01. Thereby, the magnetization can be changed easily with respect to the strain. Further, a high MR ratio is obtained in the first sample S01. Thereby, a large change of the electrical resistance is obtained. The sensitivity can be increased in the first sample S01 (e.g., the sensors 110 and 111).

Figure 4A:
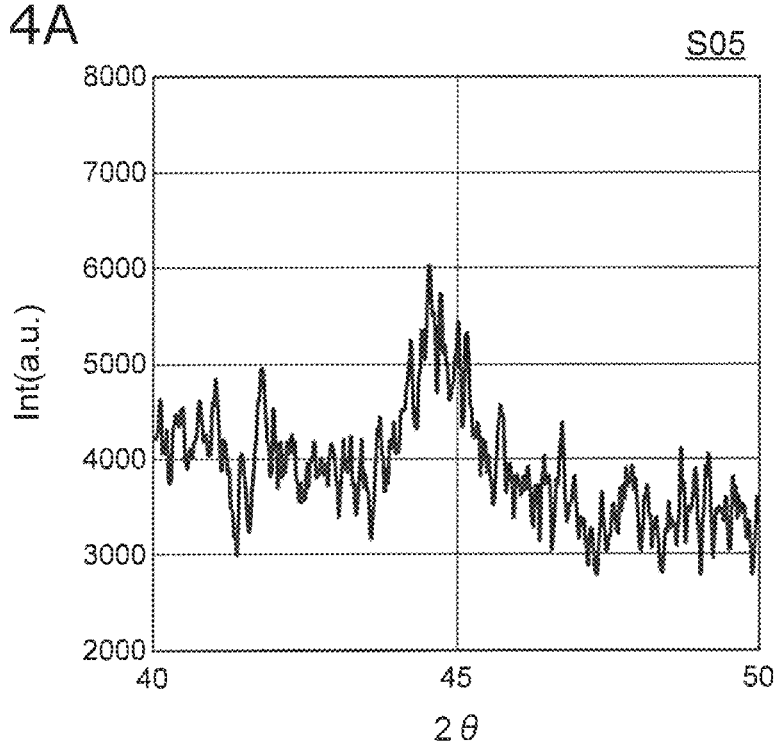
FIG. 4A and FIG. 4B are graphs illustrating characteristics of samples.
Figure 4B:
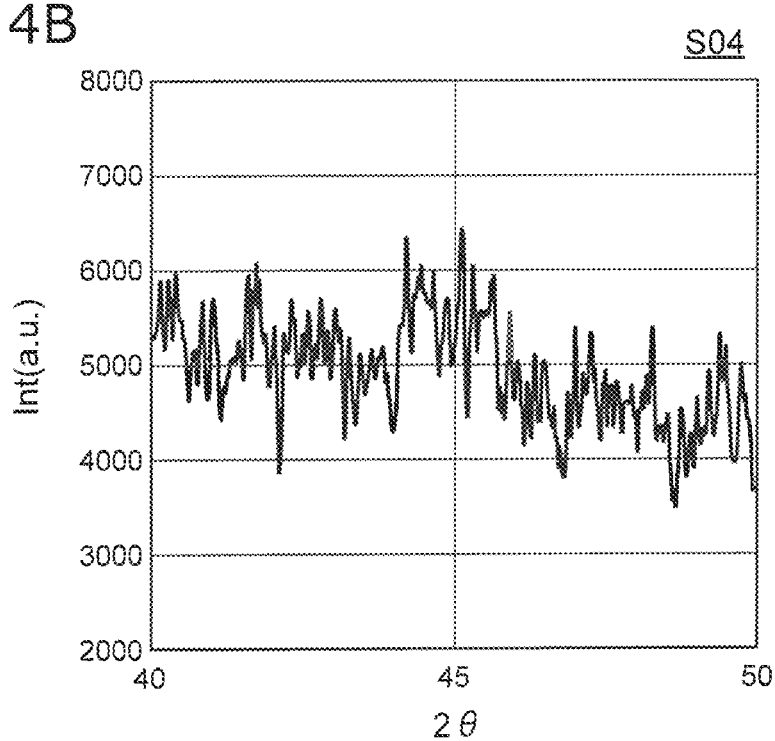

FIG. 4A and FIG. 4B are graphs illustrating characteristics of samples.

FIG. 4A and FIG. 4B respectively illustrate X-ray analysis (XRD analysis) results of a fifth sample S05 and a fourth sample S04 described below.

The fourth sample S04 has the configuration of

Si film:
Fourth film 10d: Ta (0.4 nm)
Third film 10c: Cu (0.4 nm)
First film 10a: $Co_{50}Fe_{50}$ (6.0 nm)
Film 47: Cu (1 nm)/Ta (2 nm)

The fourth sample S04 has the configuration of a portion of the first sample S01.

The fifth sample S05 is the fourth sample S04 in which the third film 10c is not provided. The fourth film 10d (the Ta film) and the first film 10a (the $Co_{50}Fe_{50}$ film) contact each other in the fifth sample S05.

In FIG. 4A and FIG. 4B, the horizontal axis is an angle 2θ of the XRD analysis. In FIG. 4A and FIG. 4B, the vertical axis is a detected intensity Int (arbitrary units).

In the fifth sample S05 as shown in FIG. 4A, a peak is observed in the intensity Int where the angle 2θ is about 44 degrees. The peak is a peak corresponding to the (110) orientation of the FeCo film. Conversely, a peak is not observed in the fourth sample S04 as shown in FIG. 4B.

In the fifth sample S05, it is considered that the coercivity Hc is large because the FeCo film has the (110) orientation. In the fourth sample S04, it is considered that the coercivity Hc is small because the FeCo film does not have the (110) orientation. Also, it is considered that the FeCo film does not have the (110) orientation in the first sample S01 which has a configuration (the fourth film 10d and the third film 10c) similar to the fourth sample S04. It is considered that this causes the coercivity Hc to be small in the first sample S01.

Thus, the (110) orientation of the FeCo film can be suppressed by providing the fourth film 10d and the third film 10c. Thereby, the coercivity Hc can be reduced.

In the fifth sample S05 as shown in FIG. 4A, the peak intensity (a first peak intensity) In the range where the angle 2θ is not less than 43 degrees and not more than 45 degrees is about 6000. The peak intensity (a second peak intensity) in the range where the angle 2θ is not less than 40 degrees and not more than 42 degrees is about 4000. In the fifth sample S05, the first peak intensity is about 1.5 times the second peak intensity.

On the other hand, in the fourth sample S04 as shown in FIG. 4B, the peak intensity (the first peak intensity) In the range where the angle 2θ is not less than 43 degrees and not more than 45 degrees is about 6400. The peak intensity (the second peak intensity) in the range where the angle 2θ is not less than 40 degrees and not more than 42 degrees is about 6000. In the fourth sample S04, the first peak intensity is about 1.1 times the second peak intensity.

In the embodiment, for example, in the X-ray analysis of the first magnetic layer 10, the first peak intensity in the range where the angle 2θ is not less than 43 degrees and not more than 45 degrees is less than 1.5 times the second peak intensity in the range where the angle 2θ is not less than 40 degrees and not more than 42 degrees. The first peak intensity may be 1.3 times the second peak intensity or less.

In the fifth sample S05 as shown in FIG. 4A, the difference (a first difference) between the maximum value and the minimum value of the intensity in the range where the angle 2θ is not less than 43 degrees and not more than 47 degrees is about 3000. The difference (a second difference) between the maximum value and the minimum value of the intensity in the range where the angle 2θ is not less than 40 degrees and not more than 42 degrees is about 2000. In the fifth sample S05, the first difference is about 1.5 times the second difference.

On the other hand, in the fourth sample S04 as shown in FIG. 4B, the difference (the first difference) between the maximum value and the minimum value of the intensity in the range where the angle 2θ is not less than 43 degrees and not more than 47 degrees is about 2500. The difference (the second difference) between the maximum value and the minimum value of the intensity in the range where the angle 2θ is not less than 40 degrees and not more than 42 degrees is about 2100. In the fifth sample S05, the first difference is about 1.2 times the second difference.

In the embodiment, for example, in the X-ray analysis of the first magnetic layer 10, the difference (the first difference) between the maximum value and the minimum value of the intensity in the range where the angle 2θ is not less than 43 degrees and not more than 47 degrees is less than about 1.5 times the difference (the second difference) between the maximum value and the minimum value of the intensity in the range where the angle 2θ is not less than 40 degrees and not more than 42 degrees. The former may be 1.3 times the latter or less.

Figure 5:
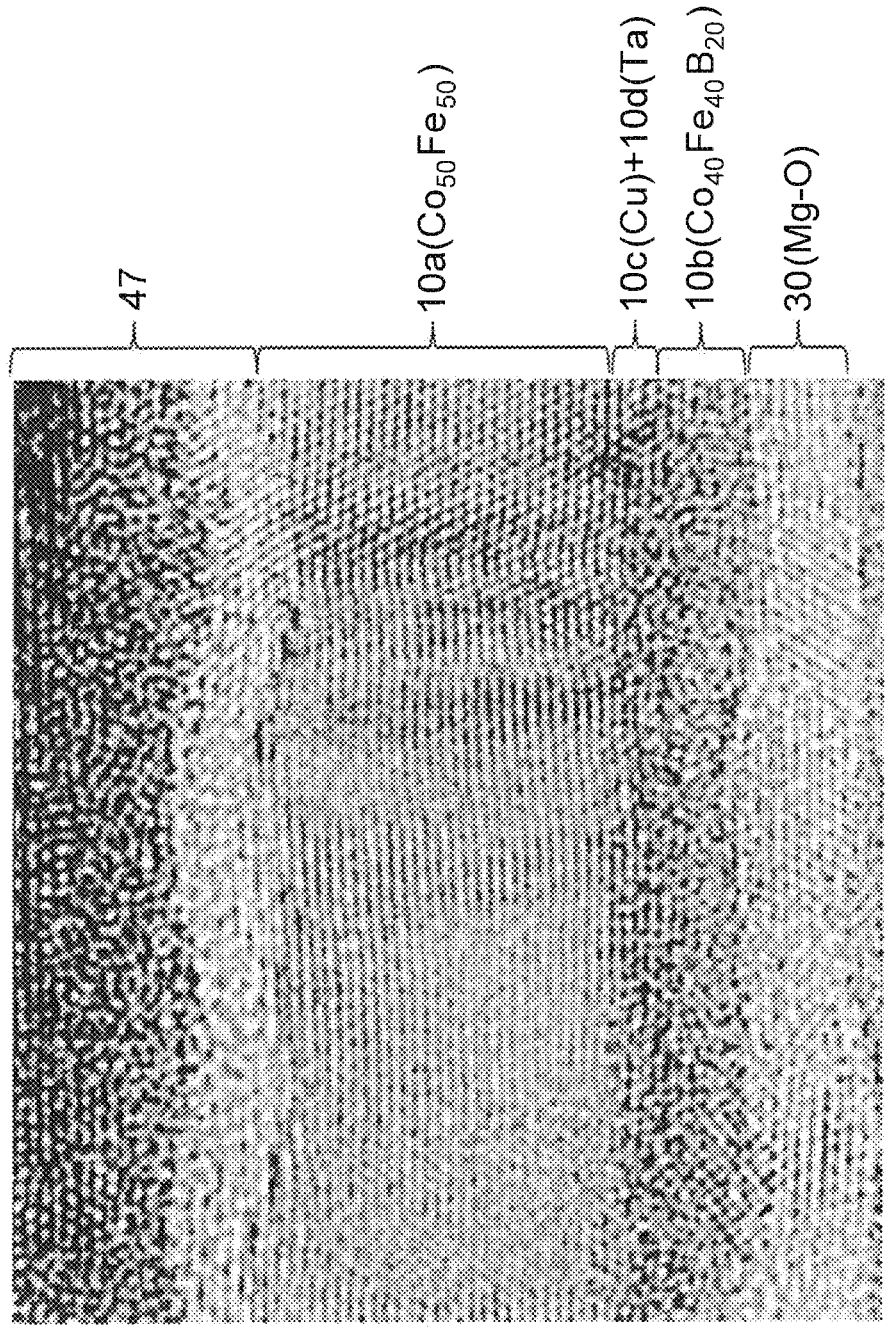
FIG. 5 is a cross-section TEM image of a sample.

FIG. 5 is a cross-section TEM image of a sample.

FIG. 5 is a cross-section TEM image of a sample having the same conditions as the fourth sample S04. As shown in FIG. 5, crystallinity is observed in the first film 10a. The crystal has a crystal orientation other than the (110) direction.

In the embodiment, the first film 10a and the second film 10b are magnetically coupled to each other. For example, the magnetization of the first film 10a and the magnetization of the second film 10b are parallel to each other.

The thickness of the third film 10c is, for example, not less than 0.1 nm and not more than 2 nm. Thereby, for example, the magnetic coupling between the first film 10a and the second film 10b is stable.

The thickness of the fourth film 10d is, for example, not less than 0.1 nm and not more than 2 nm. Thereby, for example, the magnetic coupling between the first film 10a and the second film 10b is stable.

In the embodiment, for example, the fourth film 10d contacts the second film 10b. The third film 10c contacts the first film 10a. The third film 10c contacts the fourth film 10d.

A composition ratio of Co of the first film 10a is, for example, not less than 20 atm % and not more than 80 atm %.

Thereby, for example, a high magnetostriction constant is obtained.

In the embodiment, the magnetostriction constant of the first magnetic layer 10 is, for example, $1 \times 10^{-5}$ or more.

In the embodiment, the coercivity of the first magnetic layer 10 is, for example, 80 Oe or less. The coercivity of the first magnetic layer 10 may be, for example, 50 Oe or less.

The second film 10b may further include B in addition to Fe and Co. Thereby, for example, a high MR ratio is obtained.

In the embodiment, the magnetization of the second magnetic layer 20 crosses the first direction (the Z-axis direction). The first direction is the direction from the second film 10b toward the first film 10a. The second magnetic layer 20 is, for example, an in-plane magnetization film.

Second Embodiment

Figure 6:
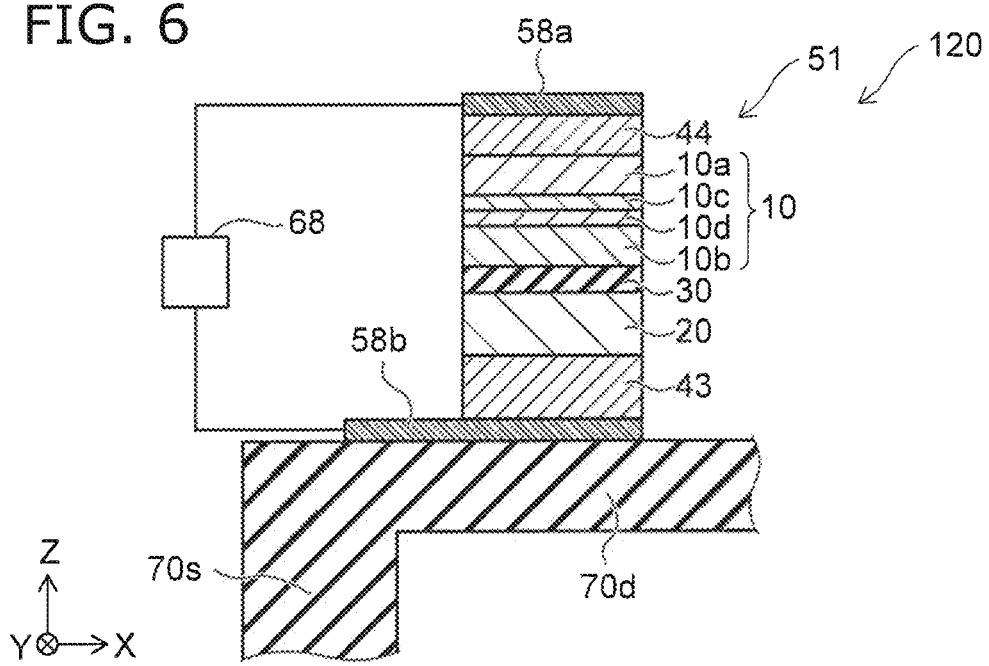
FIG. 6 is a schematic cross-sectional view illustrating a sensor according to a second embodiment.

FIG. 6 is a schematic cross-sectional view illustrating a sensor according to a second embodiment.

As shown in FIG. 6, the sensor 120 according to the embodiment also includes the film portion 70d and the first sensing element 51. The first sensing element 51 includes the third magnetic layer 43 and a fourth magnetic layer 44 in addition to the first magnetic layer 10, the second magnetic layer 20, and the first intermediate layer 30. Otherwise, the configuration of the sensor 120 can be similar to that of the sensor 110 (or the sensor 111). Examples of the third magnetic layer 43 and the fourth magnetic layer 44 will now be described.

The second magnetic layer 20 is provided between the third magnetic layer 43 and the first intermediate layer 30. The first magnetic layer 10 is provided between the fourth magnetic layer 44 and the first intermediate layer 30.

The third magnetic layer 43 and the fourth magnetic layer 44 include, for example, Mn. The third magnetic layer 43 and the fourth magnetic layer 44 include, for example, Ir—Mn.

At least one of the third magnetic layer 43 or the fourth magnetic layer 44 may include, for example, at least one selected from the group consisting of Ir—Mn, Pt—Mn, Pd—Pt—Mn, Ru—Mn, Rh—Mn, Ru—Rh—Mn, Fe—Mn, Ni—Mn, and Cr—Mn—Pt. The third magnetic layer 43 and the fourth magnetic layer 44 are, for example, antiferromagnetic layers.

For example, the third magnetic layer 43 applies a magnetic bias to the second magnetic layer 20. The magnetization of the second magnetic layer 20 is substantially fixed. For example, the third magnetic layer 43 functions as a pinned layer.

For example, the fourth magnetic layer 44 applies a magnetic bias to the first magnetic layer 10. The magnetization of the first magnetic layer 10 is controlled gradually. For example, the fourth magnetic layer 44 functions as a soft pinned layer.

For example, the magnetization of the first magnetic layer 10 is controlled gradually by the fourth magnetic layer 44. For example, the characteristics of the sensor 120 can be stable.

An experiment that relates to the sensor 120 will now be described.

Figure 7:
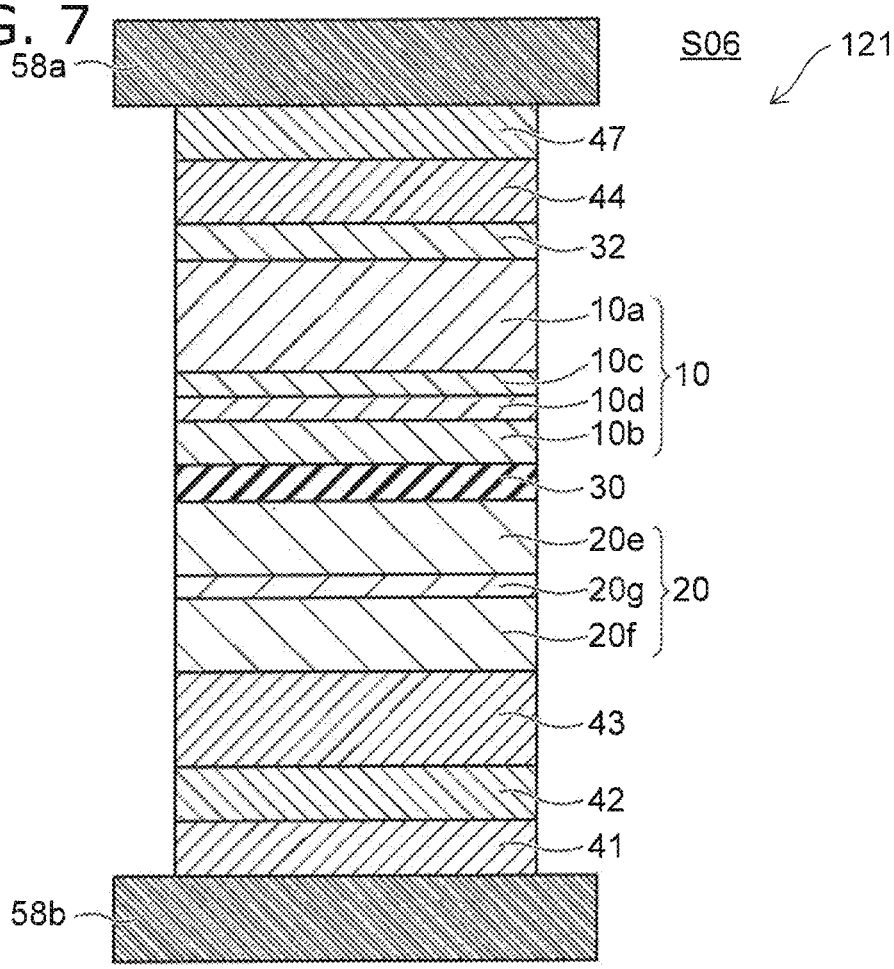
FIG. 7 is a schematic cross-sectional view illustrating an experiment sample.

FIG. 7 is a schematic cross-sectional view illustrating an experiment sample.

As shown in FIG. 7, the sixth sample S06 has the following structure. The sixth sample S06 corresponds to a sensor 121 according to the embodiment.

Film 41: Ta (1 nm)
Film 42: Ru (2 nm)
Third magnetic layer 43: $Ir_{22}Mn_{78}$ (12 nm)
Sixth film 20f: $Co_{50}Fe_{50}$ (2.5 nm)
Seventh film 20g: Ru (0.9 nm)
Fifth film 20e: $Co_{40}Fe_{40}B_{20}$ (3 nm)
First intermediate layer 30: Mg—O (1.8 nm)
Second film 10b: $Co_{40}Fe_{40}B_{20}$ (1.5 nm)
Fourth film 10d: Ta (0.4 nm)
Third film 10c: Cu (0.4 nm)
First film 10a: $Co_{50}Fe_{50}$ (6.0 nm)
Second intermediate layer 32: Cu (1 nm)
Fourth magnetic layer 44: $Ir_{22}Mn_{78}$ (4 nm)
Film 47: Cu (1 nm)/Ta (2 nm)/Ru (200 nm)

The sixth sample S06 is the first sample S01 described above in which the second intermediate layer 32 and the fourth magnetic layer 44 are further provided.

The second intermediate layer 32 is provided between the fourth magnetic layer 44 and the first film 10a. In the sixth sample S06, the thickness of the third magnetic layer 43 is 12 nm; and the thickness of the fourth magnetic layer 44 is 4 nm.

On the other hand, in a seventh sample S07, the thickness of the third magnetic layer 43 is 4 nm; and the thickness of the fourth magnetic layer 44 is 12 nm. Otherwise, the configuration of the fifth sample S05 is similar to the configuration of the sixth sample S06.

A first heat treatment, a first VSM measurement, a second heat treatment, and a second VSM measurement described below are performed for the sixth sample S06 and for the seventh sample S07. The first and second heat treatments are, for example, magnetization processing.

In the first heat treatment, a first external magnetic field along a first-axis direction is applied to the sample at a magnetization temperature of 320° C. for 1 hour. The second heat treatment is performed after the first heat treatment. In the second heat treatment, a second external magnetic field along a second-axis direction is applied to the sample at a magnetization temperature of 150° C. for 1 hour. The first external magnetic field and the second external magnetic field each are 6500 Oe. The first-axis direction and the second-axis direction are parallel to the X-Y plane and are orthogonal to each other.

The measurement when applying the external magnetic field H in the first-axis direction and the measurement when applying the external magnetic field H in the second-axis direction each are performed for the first VSM measurement and for the second VSM measurement. In these measurements, the external magnetic field H is modified in two types of ranges. In one range (a narrow range), the external magnetic field H is modified in the range of −200 Oe to +200 Oe. In another range (a wide range), the external magnetic field H is measured in the range of −5000 Oe to +5000 Oe. By measuring the external magnetic field H of two such ranges, for example, the magnetic properties of the first magnetic layer 10 applied with the magnetic bias from the fourth magnetic layer 44 and the magnetic properties of the second magnetic layer 20 applied with the magnetic bias from the third magnetic layer 43 can be evaluated.

FIGS. 8A to 8H and FIGS. 9A to 9H are graphs illustrating measurement results of the samples.

Figure 8A:
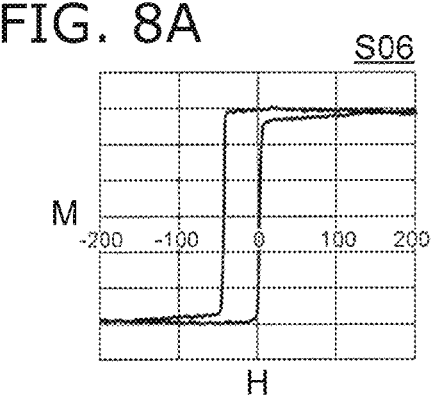
FIGS. 8A to 8H are graphs illustrating measurement results of the samples.
Figure 8B:
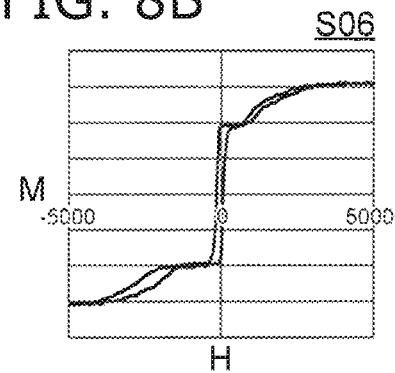
Figure 8C:
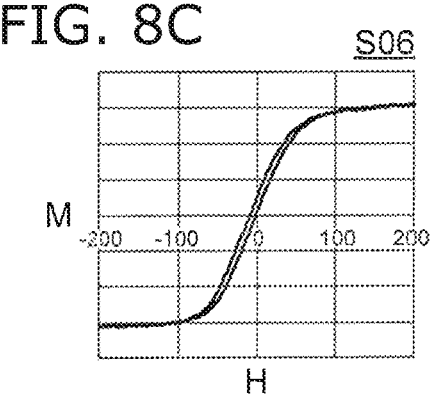
Figure 8D:
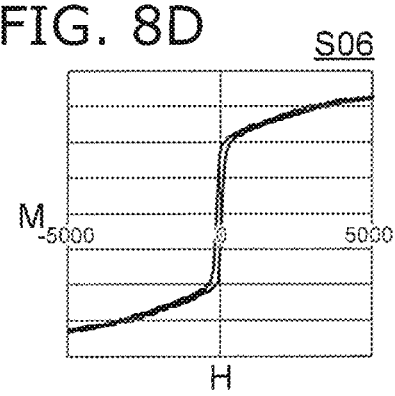
Figure 8E:
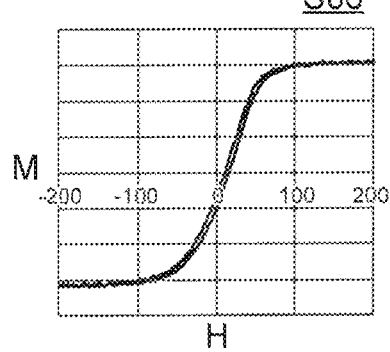
Figure 8F:
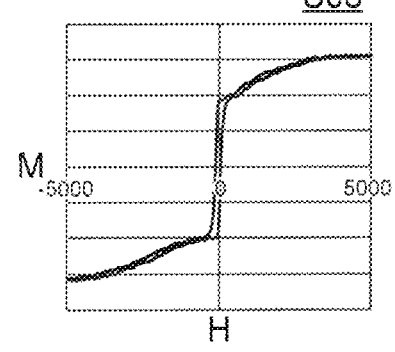
Figure 8G:
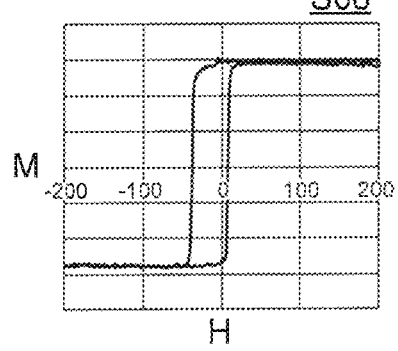
Figure 8H:
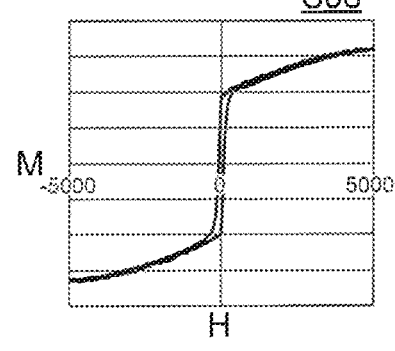
Figure 9A:
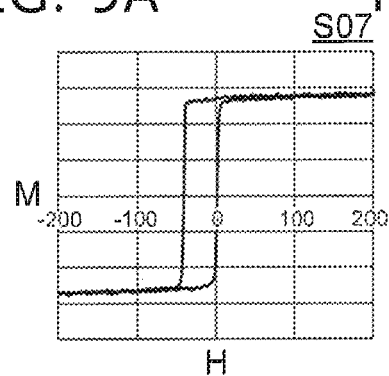
FIGS. 9A to 9H are graphs illustrating measurement results of the samples.
Figure 9B:
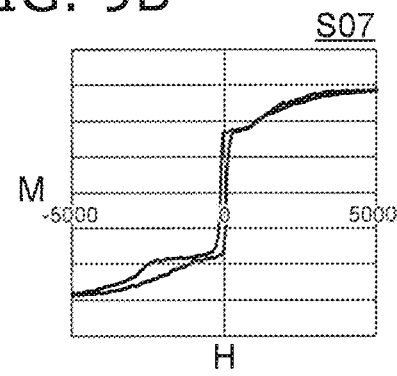
Figure 9C:
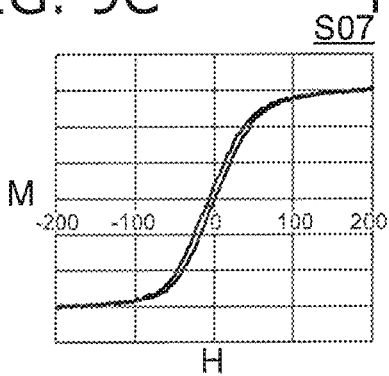
Figure 9D:
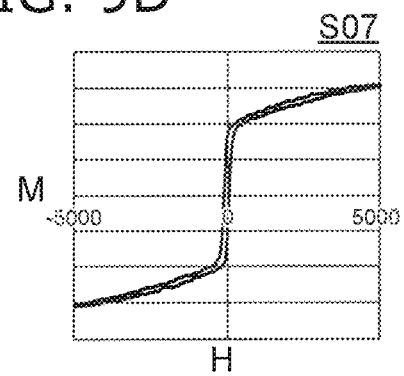
Figure 9E:
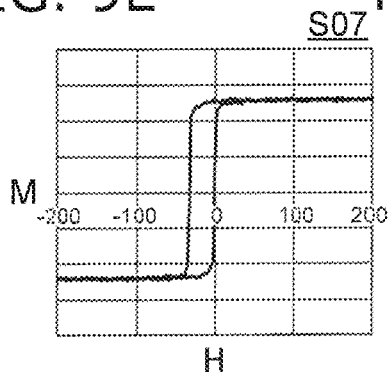
Figure 9F:
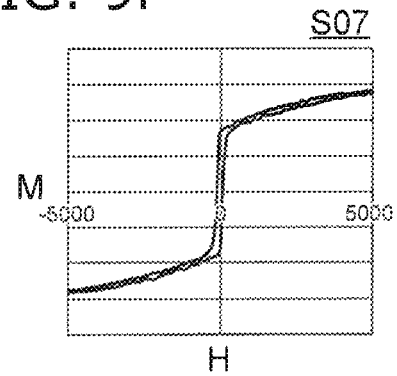
Figure 9G:
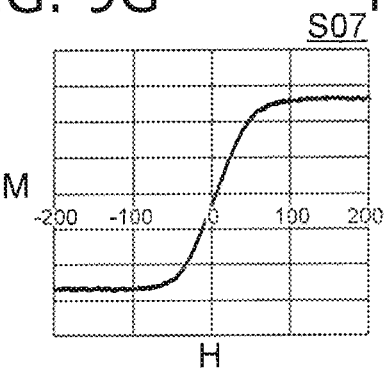
Figure 9H:
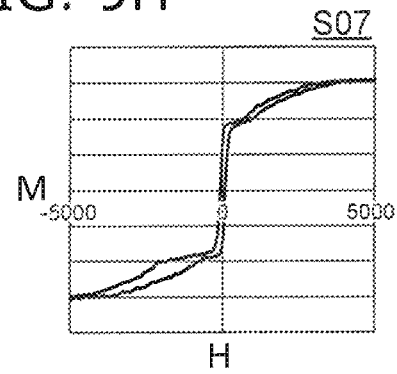

FIGS. 8A to 8H correspond to the measurements of the sixth sample S06. FIGS. 9A to 9H correspond to the measurement results of the seventh sample S07. FIG. 8A and FIG. 9A correspond to the first VSM measurement result using the external magnetic field H in the first-axis direction (the narrow range). FIG. 8B and FIG. 9B correspond to the first VSM measurement result using the external magnetic field H in the first-axis direction (the wide range). FIG. 8C and FIG. 8C correspond to the first VSM measurement result using the external magnetic field H in the second-axis direction (the narrow range). FIG. 8D and FIG. 9D correspond to the first VSM measurement result using the external magnetic field H in the second-axis direction (the wide range). FIG. 8E and FIG. 9E correspond to the second VSM measurement result using the external magnetic field H in the first-axis direction (the narrow range). FIG. 8F and FIG. 9F correspond to the second VSM measurement result using the external magnetic field H in the first-axis direction (the wide range). FIG. 8G and FIG. 9G correspond to the second VSM measurement result using the external magnetic field H in the second-axis direction (the narrow range). FIG. 8H and FIG. 9H correspond to the second VSM measurement result using the external magnetic field H in the second-axis direction (the wide range). In these figures, the horizontal axis is the external magnetic field H (Oe). The vertical axis is the magnetic moment M.

From the results of FIG. 8A to FIG. 8D, it can be seen that the easy magnetization axes of the first magnetic layer 10 and the second magnetic layer 20 are aligned with the first-axis direction.

From the results of FIG. 8E to FIG. 8H, it can be seen that the easy magnetization axis of the first magnetic layer 10 is aligned with the second-axis direction. On the other hand, it can be seen that the easy magnetization axis of the second magnetic layer 20 is aligned with the first-axis direction and is unchanged from the first VSM measurement result.

In the sixth sample S06, a first magnetic bias on the first magnetic layer 10 is generated from the fourth magnetic layer 44. On the other hand, a second magnetic bias on the second magnetic layer 20 is generated from the third magnetic layer 43. In the sixth sample S06, the orientation of the first magnetic bias changes to the second-axis direction after the second heat treatment. The orientation of the second magnetic bias does not change even after the second heat treatment.

In the sixth sample S06, the first magnetic bias can be controlled by providing the third magnetic layer 43 and the fourth magnetic layer 44 and by adjusting the orientation of the external magnetic field H of the second heat treatment. The angle between the easy magnetization axis of the first magnetic layer 10 and the easy magnetization axis of the second magnetic layer 20 can be controlled as desired.

For example, the sensitivity of the sensor can be increased by controlling the angle between the easy magnetization axis of the first magnetic layer 10 and the easy magnetization axis of the second magnetic layer 20. For example, the linear response to the input of the sensor can be improved.

From the results of FIG. 9A to FIG. 9D, it can be seen that the easy magnetization axes of the first magnetic layer 10 and the second magnetic layer 20 are aligned with the first-axis direction.

From the results of FIG. 9E to FIG. 9H, it can be seen that the easy magnetization axis of the second magnetic layer 20 is aligned with the second-axis direction. On the other hand, the easy magnetization axis of the first magnetic layer 10 is aligned with the first-axis direction and is unchanged from the first VSM measurement result.

In the seventh sample S07, the orientation of the second magnetic bias changes to the second-axis direction after the second heat treatment. The orientation of the first magnetic bias does not change even after the second heat treatment.

In the sixth sample S06, the second magnetic bias can be controlled by providing the third magnetic layer 43 and the fourth magnetic layer 44 and by adjusting the orientation of the external magnetic field H of the second heat treatment. The angle between the easy magnetization axis of the first magnetic layer 10 and the easy magnetization axis of the second magnetic layer 20 can be controlled as desired.

The angle between the easy magnetization axis of the first magnetic layer 10 and the easy magnetization axis of the second magnetic layer 20 can be controlled. For example, the sensitivity of the sensor can be increased. For example, the linear response to the input of the sensor can be improved.

For example, a low coercivity Hc is obtained for a magnetic film having high amorphousness (e.g., a Co—Fe—B alloy). In the case where a magnetic film having high amorphousness is included in the first magnetic layer 10, for example, the crystallinity of the fourth magnetic layer 44 formed on the first magnetic layer 10 is reduced. Therefore, the bias magnetic field on the first magnetic layer 10 from the fourth magnetic layer 44 easily becomes insufficient.

Conversely, by applying the structure of the first to fourth films 10a to 10d to the first magnetic layer 10, the first magnetic layer 10 is not amorphous and has crystallinity. The crystal has a crystal orientation other than the (110) direction (referring to FIG. 5). Therefore, high-quality crystallinity is obtained for the fourth magnetic layer 44 formed on the first magnetic layer 10. As a result, as described in reference to the sixth sample S06 and the seventh sample S07, the control of the angle between the two easy magnetization axes is easy.

For example, the thickness of the third magnetic layer 43 is thicker than the thickness of the fourth magnetic layer 44. The difference between the thickness of the third magnetic layer 43 and the thickness of the fourth magnetic layer 44 is, for example, 3 nm or more. Thereby, for example, the magnetization of the first magnetic layer 10 can be controlled gradually.

For example, the thickness of the fourth magnetic layer 44 is thicker than the thickness of the third magnetic layer 43. The difference between the thickness of the fourth magnetic layer 44 and the thickness of the third magnetic layer 43 is, for example, 3 nm or more. Thereby, for example, the magnetization of the second magnetic layer 20 can be controlled gradually. Thereby, a highly-sensitive strain sensor that has a linear response to the strain is obtained.

The second intermediate layer 32 may be further provided in the embodiment. The second intermediate layer 32 is provided between the first magnetic layer 10 and the fourth magnetic layer 44. The second intermediate layer 32 is nonmagnetic. The second intermediate layer 32 includes, for example, at least one selected from the group consisting of Cu, Au, Ru, Ag, Pt, Pd, Ir, Rh, Re, and Os. The second intermediate layer 32 is, for example, a Cu film that is not less than 0.8 nm and not more than 1.5 nm. For example, a magnetic field (a bias magnetic field) of a moderate strength is applicable to the first magnetic layer 10 from the fourth magnetic layer 44. For example, a sensor can be provided in which the sensitivity can be increased.

Figure 10:
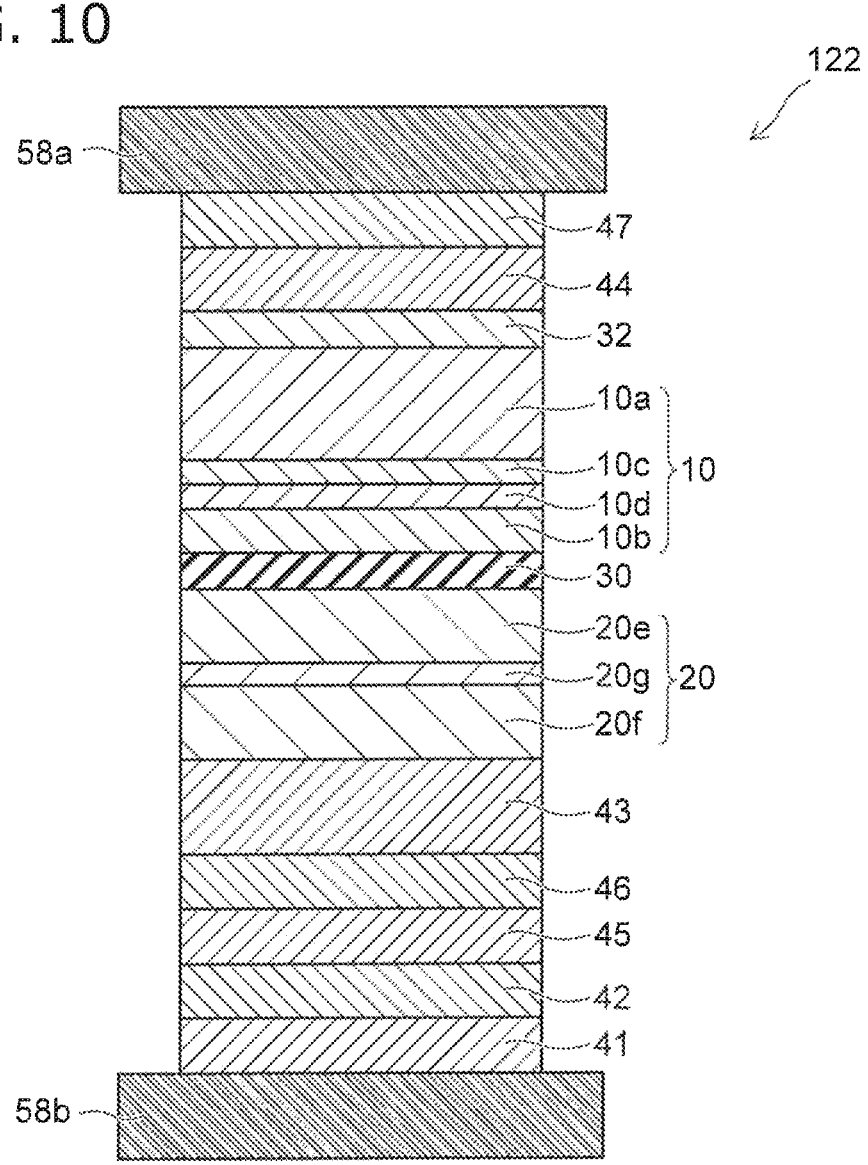
FIG. 10 is a schematic cross-sectional view illustrating a sensor according to the second embodiment.

FIG. 10 is a schematic cross-sectional view illustrating a sensor according to the second embodiment.

As shown in FIG. 10, the sensor 122 according to the embodiment further includes a film 45 and a film 46. The third magnetic layer 43 is provided between the film 45 and the second magnetic layer 20. The film 46 is provided between the film 45 and the third magnetic layer 43.

The film 45 includes, for example, $Ta_xM_{100-x}$. The film 45 may be, for example, a Ta film. The thickness of the film 45 is, for example, not less than 0.5 nm and not more than 3 nm.

The film 46 includes, for example, Ru. The thickness of the film 46 is, for example, not less than 1 nm and not more than 3 nm.

By providing such a film 45 and such a film 46, for example, the heat resistance can be improved.

Examples of the various layers (or films) included in the embodiment will now be described.

The second film 10b includes a Co—Fe—B alloy or an Fe—Co—Si—B alloy. For example, it is favorable for the boron concentration of the second film 10b to be 5 atomic % (atomic percent) or more. Thereby, an amorphous structure is easier to obtain. It is favorable for the boron concentration of the second film 10b to be 35 atomic % or less. In the case where the boron concentration is too high, for example, the magnetostriction constant decreases easily. For example, it is favorable to provide a layer of a Co—Fe—B alloy at the portion of the second film 10b on the first intermediate layer 30 side. Thereby, a high magnetoresistance effect is obtained.

For example, good crystal conformation of the second film 10b with the first intermediate layer 30 is obtained due to the fourth film 10d. A higher MR ratio is obtained.

Due to the third film 10c, for example, a crystal of the first film 10a that has the third film 10c or the film 47 as a template is obtained when annealing. For example, in the first film 10a, a low coercivity is obtained while maintaining a high magnetostriction constant.

Another film (e.g., a NiFe film) may be provided between the third film 10c and the fourth film 10d.

The first film 10a includes, for example, $Co_xFe_{100-x}$. The composition ratio x is, for example, not less than 20 atomic % and not more than 80 atomic %. A high magnetostriction coefficient is obtained easily. The composition ratio x may be, for example, not less than 30 atomic % and not more than 70 atomic %.

The first film 10a may include at least one selected from the group consisting of B, Ga, Al, Si, Tb, and W. For example, a high magnetostriction constant is easier to obtain. For example, a low coercivity is easier to obtain.

At least one of the third magnetic layer 43 or the fourth magnetic layer 44 includes, for example, Mn. The composition ratio of Mn in at least one of the third magnetic layer 43 or the fourth magnetic layer 44 is, for example, 70% or more.

In the case where the fourth magnetic layer 44 includes IrMn, the thickness of the fourth magnetic layer 44 is, for example, not less than 4 nm and not more than 20 nm.

In the case where the third magnetic layer 43 includes IrMn, the thickness of the third magnetic layer 43 is, for example, not less than 4 nm and not more than 20 nm.

In the manufacturing processes of the sensor according to the embodiment, the angle between the magnetization of the first film 10a and the magnetization of the second film 10b can be controlled by the first processing and the second processing recited above.

The magnetization temperature of an antiferromagnetic layer is different according to the type and the thickness of the antiferromagnetic material. For example, the magnetization temperature of an antiferromagnetic layer including Pt is higher than the magnetization temperature of an antiferromagnetic layer including Ir. For example, in the case of the same antiferromagnetic material, the magnetization temperature of a thick antiferromagnetic layer is higher than the magnetization temperature of a thin antiferromagnetic layer.

In the case where the antiferromagnetic material of the third magnetic layer 43 and the antiferromagnetic material of the third magnetic layer 43 are different from each other, the angle between the orientation of the magnetization of the second magnetic layer 20 and the orientation of the magnetization of the first film 10a can be adjusted by the first processing and the second processing. For example, the sensitivity of the sensor can be controlled. For example, the linearity of the response of the sensor can be controlled.

For example, the temperature of the first processing is higher than the magnetization temperature of the third magnetic layer 43 and the magnetization temperature of the fourth magnetic layer 44. The temperature of the second processing is between the magnetization temperature of the third magnetic layer 43 and the magnetization temperature of the fourth magnetic layer 44. For example, the temperature of the first processing is 320° C. The temperature of the second processing is 150° C. The direction of the external magnetic field of the first processing crosses the direction of the external magnetic field of the second processing.

The film 41 includes, for example, Ta. The thickness of the film 41 is not less than 1 nm and not more than 10 nm. The film 42 includes, for example, Ru. The thickness of the film 42 is not less than 2 nm and not more than 10 nm. The total thickness of the film 41 and the film 42 is, for example, not less than 4 nm and not more than 20 nm.

The film 42 may be, for example, a Ru layer having a hexagonal close-packed (hcp) structure. The film 42 may be, for example, a NiFe layer having a face-centered cubic (fcc) structure, a Cu layer having a fcc structure, or a Cr layer having a body-centered cubic (bcc) structure.

As recited above, the second magnetic layer 20 may include the fifth film 20e, the sixth film 20f, and the seventh film 20g. The sixth film 20f includes, for example, FeCo. The thickness of the sixth film 20f is, for example, not less than 2 nm and not more than 4 nm. The seventh film 20g includes, for example, Ru. The thickness of the seventh film 20g is, for example, not less than 0.7 nm and not more than 1 nm. The fifth film 20e includes, for example, CoFeB. The thickness of the fifth film 20e is, for example, not less than 2 nm and not more than 4 nm.

The second magnetic layer 20 may be one magnetic film. In such a case, the second magnetic layer 20 includes, for example, at least one selected from the group consisting of Co, Fe, and Ni. The second magnetic layer 20 is, for example, a $Co_xFe_{100-x}$ alloy layer (0 atomic %≤x≤100 atomic %). Or, the second magnetic layer 20 may be a $Ni_xFe_{100-x}$ alloy layer (0 atomic %≤x≤100 atomic %). A nonmagnetic element may be added to these materials. The thickness of the second magnetic layer 20 is, for example, not less than 1.5 nm and not more than 5 nm.

The first intermediate layer 30 includes, for example, at least one selected from the group consisting of MgO, $Al_2O_3$, TiO, ZnO, and Ga—O. The thickness of the first intermediate layer 30 is, for example, not less than 0.6 nm and not more than 5 nm.

At least one of the first electrode 58a or the second electrode 58b includes, for example, at least one selected from the group consisting of aluminum (Al), aluminum copper alloy (Al—Cu), copper (Cu), silver (Ag), tantalum (Ta), and gold (Au). At least one of the first electrode 58a or the second electrode 58b may include, for example, at least one selected from the group consisting of TaMo, Ti, and TiN.

Multiple sensing elements may be provided in the embodiment.

FIG. 11A to FIG. 11D are schematic views illustrating a sensor according to the embodiment.

Figure 11A:
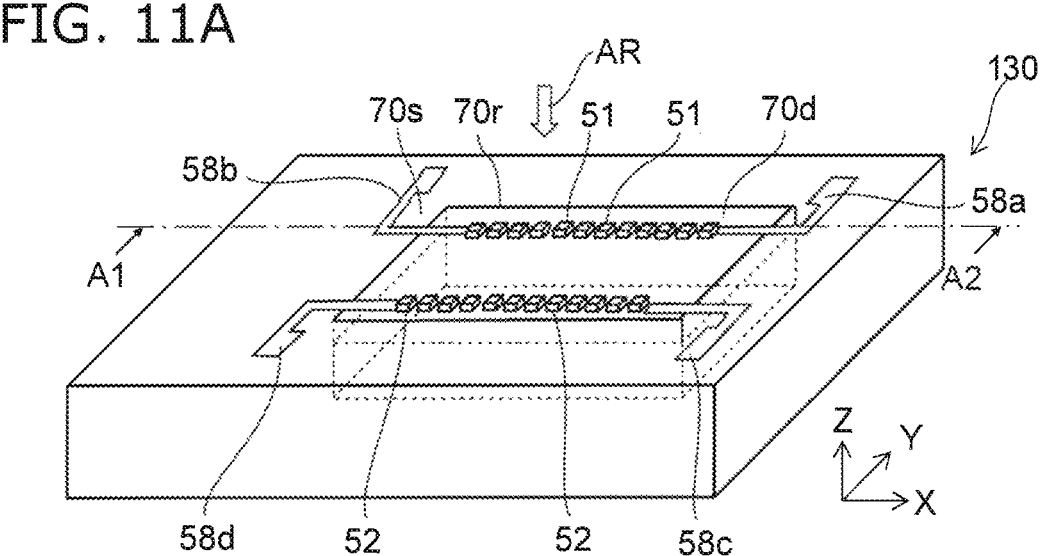
FIG. 11A to FIG. 11D are schematic views illustrating a sensor according to the embodiment.
Figure 11B:
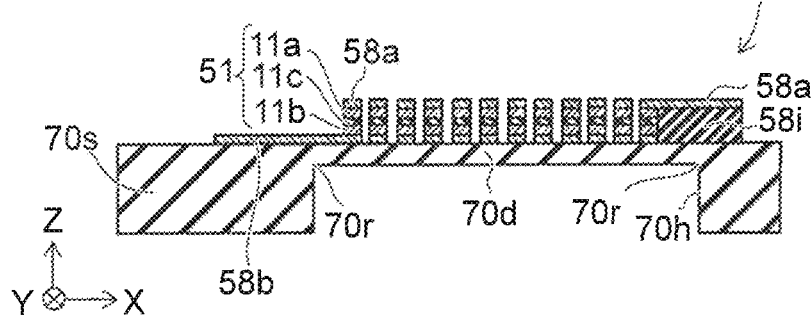
Figure 11D:
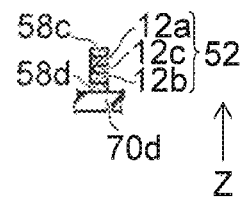
Figure 11C:
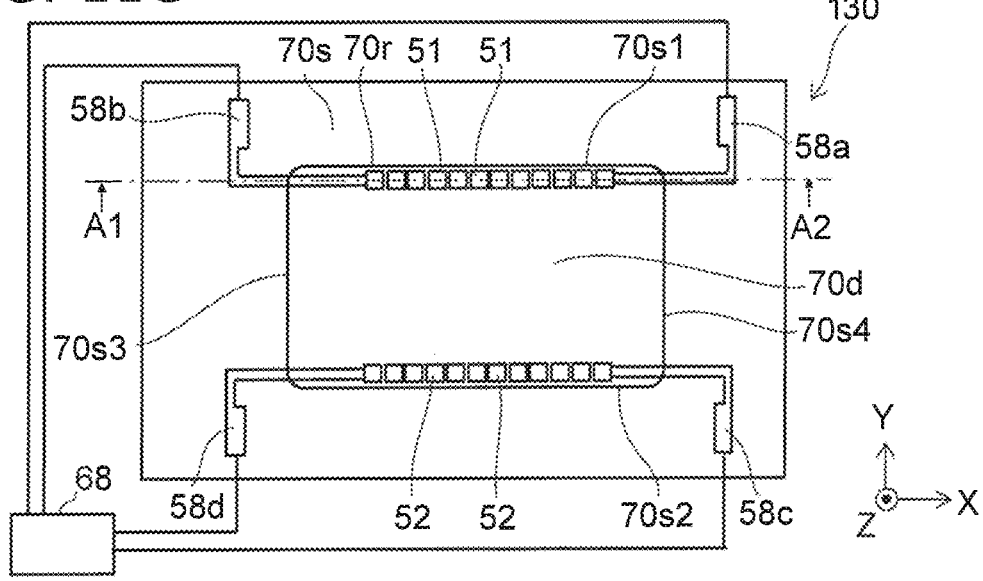

FIG. 11A is a perspective view. FIG. 11B is a line A1-A2 cross-sectional view of FIG. 11A. FIG. 11C is a plan view as viewed along arrow AR of FIG. 11A. FIG. 11D is a cross-sectional view illustrating a portion of the sensor.

As shown in FIG. 11A, the sensor 130 according to the embodiment includes the film portion 70d, the first sensing element 51, and a second sensing element 52.

The first sensing element 51 and the second sensing element 52 are fixed to the film portion 70d. In the example, the first sensing element 51 is fixed to a first position (a first region) of the film portion 70d. The second sensing element 52 is fixed to a second position (a second region) of the film portion 70d.

The multiple first sensing elements 51 and the multiple second sensing elements 52 are provided in the example. In the example, the multiple first sensing elements 51 are arranged along the X-axis direction. In the example, the multiple second sensing elements 52 are arranged along the X-axis direction. For example, the multiple first sensing elements 51 are connected in series to each other. For example, the multiple second sensing elements 52 are connected in series to each other. In the embodiment, the number of the first sensing elements 51 is arbitrary. The number of the second sensing elements 52 is arbitrary.

The film portion 70d is held by the supporter 70s. The film portion 70d has an outer edge 70r. The supporter 70s holds the outer edge 70r. For example, a substrate that is used to form the supporter 70s and the film portion 70d is provided. The substrate is, for example, a silicon substrate. A hollow 70h is provided in the substrate by removing a portion of the substrate (referring to FIG. 11B). The thin portion of the substrate is used to form the film portion 70d. The thick portion of the substrate is used to form the supporter 70s.

As shown in FIG. 11B, the first sensing element 51 includes a first magnetic film 11a, a first opposing magnetic film 11b, and a first intermediate film 11c. The first intermediate film 11c is provided between the first magnetic film 11a and the first opposing magnetic film 11b. The second sensing element 52 includes a second magnetic film 12a, a second opposing magnetic film 12b, and a second intermediate film 12c. The second intermediate film 12c is provided between the second magnetic film 12a and the second opposing magnetic film 12b.

For example, the first magnetic film 11a and the second magnetic film 12a correspond to the first magnetic layer 10. For example, the first opposing magnetic film 11b and the second opposing magnetic film 12b correspond to the second magnetic layer 20. For example, the first intermediate film 11c and the second intermediate film 12c correspond to the first intermediate layer 30.

For example, the first electrode 58a and the second electrode 58b are provided as illustrated in FIG. 11B. For example, the first magnetic film 11a, the first opposing magnetic film 11b, and the first intermediate film 11c are arranged between the first electrode 58a and the second electrode 58b.

For example, a third electrode 58c and a fourth electrode 58d are provided as illustrated in FIG. 11D. For example, the second magnetic film 12a, the second opposing magnetic film 12b, and the second intermediate film 12c are arranged between the third electrode 58c and the fourth electrode 58d.

In the example as illustrated in FIG. 11B, an insulating layer 58*i* is provided between the first electrode 58*a* and the film portion 70*d*. For example, the insulating layer 58*i* is provided also between the first electrode 58*a* and the second electrode 58*b*. For example, the insulating layer 58*i* is provided also between the third electrode 58*c* and the fourth electrode 58*d*. Electrical insulation between the electrodes is obtained using the insulating layer 58*i*.

As shown in FIG. 11C, the sensor 130 may further include the processor 68 (e.g., a processing circuit). The processor 68 is electrically connected to the first sensing element 51 and the second sensing element 52. For example, the processor 68 is electrically connected to the first electrode 58*a*, the second electrode 58*b*, the third electrode 58*c*, and the fourth electrode 58*d*. The processor 68 outputs a signal corresponding to a signal obtained from the first sensing elements 51. The processor 68 outputs a signal corresponding to a signal obtained from the second sensing elements 52. The processor 68 outputs a signal corresponding to the change of the electrical resistance occurring in the sensing elements.

In the example as shown in FIG. 11C, the film portion 70*d* (the outer edge 70*r*) is substantially a polygon (a quadrilateral, and specifically, a rectangle). The outer edge 70*r* of the film portion 70*d* includes a first side 70*s*1, a second side 70*s*2, a third side 70*s*3, and a fourth side 70*s*4.

Various configurations are applicable to the film portion 70*d* (the outer edge 70*r*). For example, the film portion 70*d* (the outer edge 70*r*) may have substantially a perfect circle configuration, may have a flattened circular configuration (including an elliptical configuration), may have a substantially square configuration, or may have a rectangular configuration. For example, in the case where the film portion 70*d* (the outer edge 70*r*) has a substantially square configuration or a substantially rectangular configuration, the portions at the four corners (the corner portions) may have curved configurations.

The first side 70*s*1 extends in a first direction (in the example, the X-axis direction). The second side 70*s*2 is separated from the first side 70*s*1 in a second direction. The second direction crosses the first direction. In the example, the second direction is the Y-axis direction. The second side 70*s*2 extends in the first direction (the X-axis direction). The third side 70*s*3 extends in the second direction (the Y-axis direction). The fourth side 70*s*4 is separated from the third side 70*s*3 in the first direction (the X-axis direction) and extends in the second direction (the Y-axis direction).

In the example, the distance along the first direction between the third side 70*s*3 and the fourth side 70*s*4 is longer than the distance along the second direction between the first side 70*s*1 and the second side 70*s*2. The film portion 70*d* is substantially a rectangle; and the first side 70*s*1 and the second side 70*s*2 are the long sides. The third side 70*s*3 and the fourth side 70*s*4 are the short sides.

When stress is applied to the film portion 70*d*, a large strain (an anisotropic strain) is generated at the vicinity of the outer edge 70*r* of the film portion 70*d*. By arranging the sensing elements at the vicinity of the outer edge 70*r* of the film portion 70*d*, a large strain is applied to the sensing elements; and high sensitivity is obtained.

In the example, the multiple first sensing elements 51 are arranged along the first side 70*s*1. The multiple second sensing elements 52 are arranged along the second side 70*s*2.

The SN ratio can be improved by connecting the multiple sensing elements in series. In the embodiment, the multiple sensing elements that obtain electrical signals of the same polarity when the pressure is applied can be arranged. Thereby, the SN ratio improves.

The embodiment may include an electronic device. The electronic device includes, for example, the sensors according to the embodiments recited above and the sensors of modifications of the embodiments recited above. The electronic device includes, for example, an information terminal. The information terminal includes a recorder, etc. The electronic device includes a microphone, a blood pressure sensor, a touch panel, etc.

Figure 12:
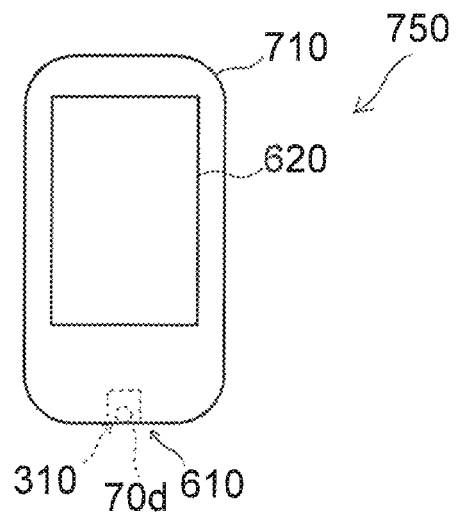
FIG. 12 is a schematic view illustrating an electronic device according to the embodiment.

FIG. 12 is a schematic view illustrating an electronic device according to the embodiment.

As shown in FIG. 12, the electronic device 750 according to the embodiment is, for example, an information terminal 710. For example, a microphone 610 is provided in the information terminal 710.

The microphone 610 includes, for example, a sensor 310. For example, the film portion 70*d* is substantially parallel to a surface where a displayer 620 of the information terminal 710 is provided. The arrangement of the film portion 70*d* is arbitrary. Any sensor described in reference to the embodiments recited above is applicable to the sensor 310.

Figures 13A, 13B:
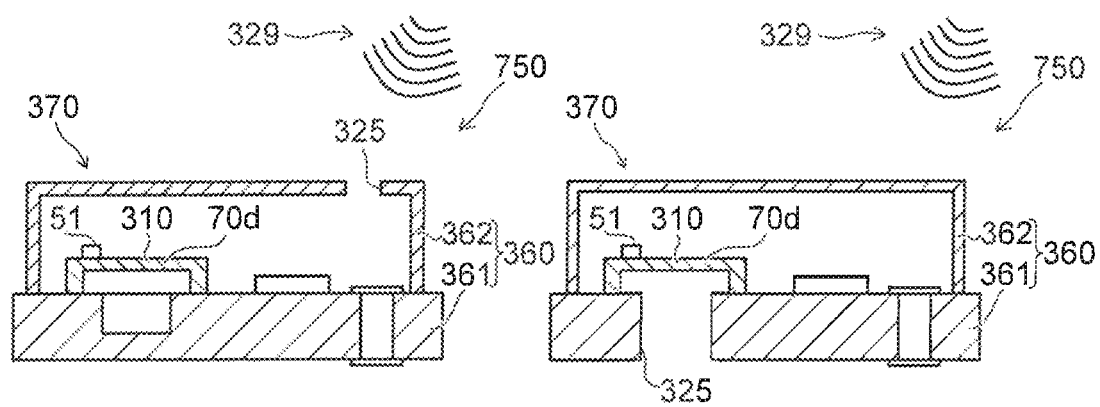
FIG. 13A and FIG. 13B are schematic cross-sectional views illustrating the electronic device according to the embodiment.

FIG. 13A and FIG. 13B are schematic cross-sectional views illustrating the electronic device according to the embodiment.

As shown in FIG. 13A and FIG. 13B, the electronic device 750 (e.g., a microphone 370 (an acoustic microphone)) includes a housing 360, a cover 362, and the sensor 310. The housing 360 includes, for example, a substrate 361 (e.g., a printed circuit board) and the cover 362. The substrate 361 includes, for example, a circuit such as an amplifier, etc.

An acoustic hole 325 is provided in the housing 360 (at least one of the substrate 361 or the cover 362). In the example shown in FIG. 33B, the acoustic hole 325 is provided in the cover 362. In the example shown in FIG. 33B, the acoustic hole 325 is provided in the substrate 361. Sound 329 passes through the acoustic hole 325 and enters the interior of the cover 362. The microphone 370 responds to the sound pressure.

For example, the sensor 310 is placed on the substrate 361; and an electrical signal line (not illustrated) is provided. The cover 362 is provided to cover the sensor 310. The housing 360 is provided around the sensor 310. At least a portion of the sensor 310 is provided inside the housing 360. For example, the first sensing element 51 and the film portion 70*d* are provided between the substrate 361 and the cover 362. For example, the sensor 310 is provided between the substrate 361 and the cover 362.

Figure 14A:
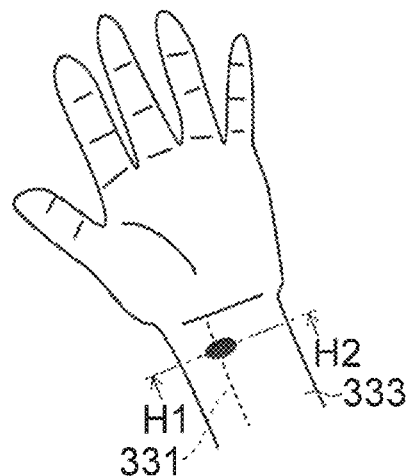
FIG. 14A and FIG. 14B are schematic views illustrating another electronic device according to the embodiment.
Figure 14B:
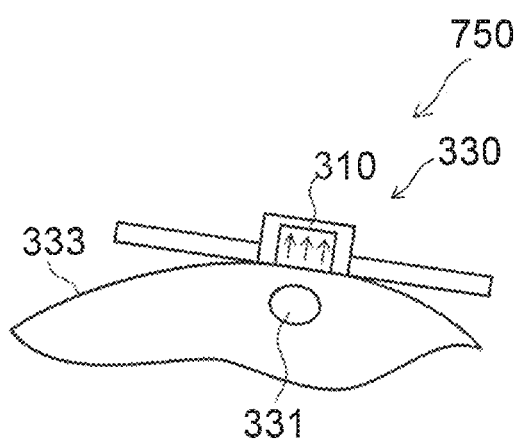

FIG. 14A and FIG. 14B are schematic views illustrating another electronic device according to the embodiment.

In the example of these drawings, the electronic device 750 is a blood pressure sensor 330. FIG. 14A is a schematic plan view illustrating skin on an arterial vessel of a human. FIG. 14B is a line H1-H2 cross-sectional view of FIG. 14A.

The sensor 310 is used as the sensor in the blood pressure sensor 330. The sensor 310 contacts the skin 333 on the arterial vessel 331. Thereby, the blood pressure sensor 330 can continuously perform blood pressure measurements.

Figure 15:
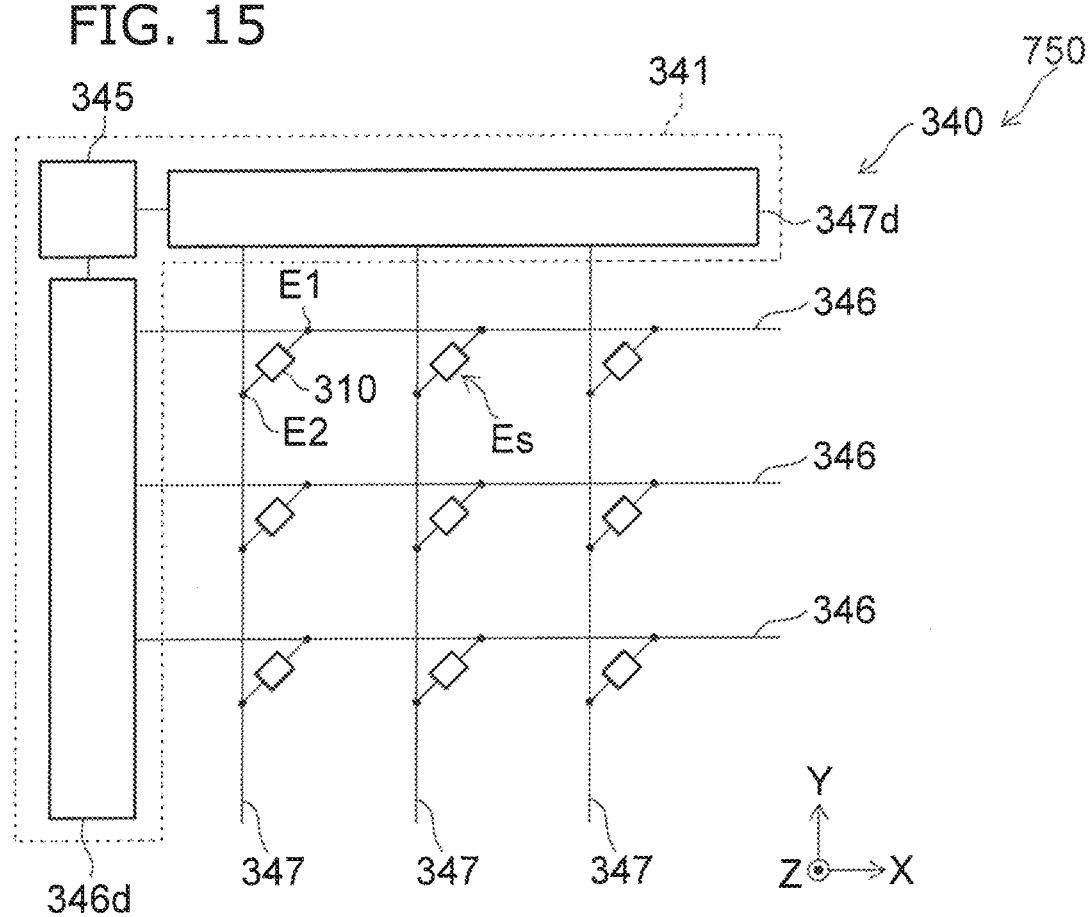
FIG. 15 is a schematic view illustrating another electronic device according to the embodiment.

FIG. 15 is a schematic view illustrating another electronic device according to the embodiment.

In the example of the drawing, the electronic device 750 is a touch panel 340. In the touch panel 340, the sensors 310 are provided in at least one of the interior of the display or the exterior of the display.

For example, the touch panel 340 includes multiple first interconnects 346, multiple second interconnects 347, the multiple sensors 310, and a control circuit 341.

In the example, the multiple first interconnects 346 are arranged along the Y-axis direction. Each of the multiple first interconnects 346 extends along the X-axis direction. The multiple second interconnects 347 are arranged along the X-axis direction. Each of the multiple second interconnects 347 extends along the Y-axis direction.

One of the multiple sensors 310 is provided at the crossing portion between the multiple first interconnects 346 and the multiple second interconnects 347. One of the sensors 310 is used as one of sensing components Es for sensing. The crossing portion includes the position where the first interconnect 346 and the second interconnect 347 cross and includes the region at the periphery of the position.

One end E1 of one of the multiple sensors 310 is connected to one of the multiple first interconnects 346. Another end E2 of the one of the multiple sensors 310 is connected to one of the multiple second interconnects 347.

The control circuit 341 is connected to the multiple first interconnects 346 and the multiple second interconnects 347. For example, the control circuit 341 includes a first interconnect circuit 346d that is connected to the multiple first interconnects 346, a second interconnect circuit 347d that is connected to the multiple second interconnects 347, and a control signal circuit 345 that is connected to the first interconnect circuit 346d and the second interconnect circuit 347d.

According to the embodiment, an electronic device that uses a sensor in which the sensitivity can be increased can be provided.

The embodiments may include the following configurations (technological proposals).

Configuration 1
A sensor, comprising:
a film portion, the film portion being deformable; and
a first sensing element provided at the film portion,
the first sensing element including
a first magnetic layer,
a second magnetic layer, and
a first intermediate layer provided between the first magnetic layer and the second magnetic layer, the first intermediate layer being nonmagnetic,
the first magnetic layer including
a first film including Fe and Co,
a second film including Fe and Co,
a third film including at least one selected from the group consisting of Cu, Au, Ru, Ag, Pt, Pd, Ir, Rh, Re, and Os and being provided between the first film and the second film, and
a fourth film including at least one selected from the group consisting of Mg, Ca, Sc, Ti, Sr, Y, Zr, Nb, Mo, Ba, La, Hf, Ta, and W and being provided between the third film and the second film.

Configuration 2
The sensor according to Configuration 1, wherein an electrical resistance of the first sensing element changes according to a deformation of the film portion.

Configuration 3
The sensor according to Configuration 1 or 2, wherein a first peak intensity is less than 1.5 times a second peak intensity in an X-ray analysis of the first magnetic layer, the first peak intensity being in a range where an angle 2θ is not less than 43 degrees and not more than 45 degrees, the second peak intensity being in a range where the angle 2θ is not less than 40 degrees and not more than 42 degrees.

Configuration 4
The sensor according to Configuration 3, wherein the first peak intensity is 1.3 times the second peak intensity or less.

Configuration 5
The sensor according to Configuration 1 or 2, wherein a first difference is less than 1.5 times a second difference in an X-ray analysis of the first magnetic layer, the first difference being between a maximum value and a minimum value of an intensity in a range where an angle 2θ is not less than 43 degrees and not more than 47 degrees, the second difference being between a maximum value and a minimum value of an intensity in a range where the angle 2θ is not less than 40 degrees and not more than 42 degrees.

Configuration 6
The sensor according to Configuration 4, wherein the first difference is 1.3 times the second difference or less.

Configuration 7
The sensor according to any one of Configurations 1 to 6, wherein a thickness of the third film is not less than 0.1 nm and not more than 2 nm.

Configuration 8
The sensor according to any one of Configurations 1 to 7, wherein a thickness of the fourth film is not less than 0.1 nm and not more than 2 nm.

Configuration 9
The sensor according to any one of Configurations 1 to 8, wherein the fourth film contacts the second film.

Configuration 10
The sensor according to any one of Configurations 1 to 9, wherein the third film contacts the first film.

Configuration 11
The sensor according to any one of Configurations 1 to 10, wherein the third film contacts the fourth film.

Configuration 12
The sensor according to any one of Configurations 1 to 11, wherein a composition ratio of Co of the first film is not less than 20 atm % and not more than 80 atm %.

Configuration 13
The sensor according to any one of Configurations 1 to 12, wherein the second film further includes B.

Configuration 14
The sensor according to any one of Configurations 1 to 13, wherein a magnetostriction constant of the first magnetic layer is $1 \times 10^{-5}$ or more.

Configuration 15
The sensor according to any one of Configurations 1 to 14, wherein a coercivity of the first magnetic layer is 80 Oe or less.

Configuration 16
The sensor according to any one of Configurations 1 to 15, wherein a magnetization of the second magnetic layer crosses a first direction from the second film toward the first film.

Configuration 17
The sensor according to any one of Configurations 1 to 16, wherein an orientation of a magnetization of the second magnetic layer changes less easily than an orientation of a magnetization of the first magnetic layer.

Configuration 18
The sensor according to any one of Configurations 1 to 17, further comprising:
a third magnetic layer including Mn; and
a fourth magnetic layer including Mn,
the second magnetic layer being provided between the third magnetic layer and the first intermediate layer,
the first magnetic layer being provided between the fourth magnetic layer and the first intermediate layer.

Configuration 19

The sensor according to Configuration 18, wherein a difference between a thickness of the third magnetic layer and a thickness of the fourth magnetic layer is 3 nm or more.

Configuration 20

The sensor according to Configuration 18 or 19, further comprising a second intermediate layer provided between the first magnetic layer and the fourth magnetic layer, the second intermediate layer being nonmagnetic, the second intermediate layer including at least one selected from the group consisting of Cu, Au, Ru, Ag, Pt, Pd, Ir, Rh, Re, and Os.

Configuration 21

A microphone, comprising the sensor according to any one of Configurations 1 to 20.

Configuration 22

A blood pressure sensor, comprising the sensor according to any one of Configurations 1 to 20.

Configuration 23

A touch panel, comprising the sensor according to any one of Configurations 1 to 20.

According to the embodiments, a sensor, a microphone, a blood pressure sensor, and a touch panel are provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as film portions, sensing elements, magnetic layers, intermediate layers, films, electrodes, processors, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, microphones, blood pressure sensors, and touch panels practicable by an appropriate design modification by one skilled in the art based on the sensors, the microphones, the blood pressure sensors, and the touch panels described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a film portion, the film portion being deformable; and
a first sensing element provided at the film portion,
the first sensing element including
a first magnetic layer,
a second magnetic layer, and
a first intermediate layer provided between the first magnetic layer and the second magnetic layer, the first intermediate layer being nonmagnetic,
the first magnetic layer including
a first film including Fe and Co,
a second film including Fe and Co,
a third film including at least one selected from the group consisting of Cu, Au, Ru, Ag, Pt, Pd, Ir, Rh, Re, and Os and being provided between the first film and the second film, and
a fourth film including at least one selected from the group consisting of Mg, Ca, Sc, Ti, Sr, Y, Zr, Nb, Mo, Ba, La, Hf, Ta, and W and being provided between the third film and the second film.

2. The sensor according to claim 1, wherein an electrical resistance of the first sensing element changes according to a deformation of the film portion.

3. The sensor according to claim 1, wherein a first peak intensity is less than 1.5 times a second peak intensity in an X-ray analysis of the first magnetic layer, the first peak intensity being in a range where an angle 2θ is not less than 43 degrees and not more than 45 degrees, the second peak intensity being in a range where the angle 2θ is not less than 40 degrees and not more than 42 degrees.

4. The sensor according to claim 3, wherein the first peak intensity is 1.3 times the second peak intensity or less.

5. The sensor according to claim 1, wherein a first difference is less than 1.5 times a second difference in an X-ray analysis of the first magnetic layer, the first difference being between a maximum value and a minimum value of an intensity in a range where an angle 2θ is not less than 43 degrees and not more than 47 degrees, the second difference being between a maximum value and a minimum value of an intensity in a range where the angle 2θ is not less than 40 degrees and not more than 42 degrees.

6. The sensor according to claim 4, wherein the first difference is 1.3 times the second difference or less.

7. The sensor according to claim 1, wherein a thickness of the third film is not less than 0.1 nm and not more than 2 nm.

8. The sensor according to claim 1, wherein a thickness of the fourth film is not less than 0.1 nm and not more than 2 nm.

9. The sensor according to claim 1, wherein the fourth film contacts the second film.

10. The sensor according to claim 1, wherein the third film contacts the first film.

11. The sensor according to claim 1, wherein the third film contacts the fourth film.

12. The sensor according to claim 1, wherein a composition ratio of Co of the first film is not less than 20 atm % and not more than 80 atm %.

13. The sensor according to claim 1, wherein the second film further includes B.

14. The sensor according to claim 1, wherein a magnetization of the second magnetic layer crosses a first direction from the second film toward the first film.

15. The sensor according to claim 1, further comprising:
a third magnetic layer including Mn; and
a fourth magnetic layer including Mn, the second magnetic layer being provided between the third magnetic layer and the first intermediate layer, the first magnetic layer being provided between the fourth magnetic layer and the first intermediate layer.

16. The sensor according to claim 15, wherein a difference between a thickness of the third magnetic layer and a thickness of the fourth magnetic layer is 3 nm or more.

17. The sensor according to claim 15, further comprising a second intermediate layer provided between the first magnetic layer and the fourth magnetic layer, the second intermediate layer being nonmagnetic, the second intermediate layer including at least one selected from the group consisting of Cu, Au, Ru, Ag, Pt, Pd, Ir, Rh, Re, and Os.

18. A microphone, comprising the sensor according to claim 1.

19. A touch panel, comprising the sensor according to claim 1.

\* \* \* \* \*